United States Patent [19]
Klippel

[11] 3,942,521
[45] Mar. 9, 1976

[54] EXTENSION SPLINT
[75] Inventor: Allen Pummill Klippel, Clayton, Mo.
[73] Assignee: Rescue Products, Inc., Bridgeton, Mo.
[22] Filed: Aug. 6, 1974
[21] Appl. No.: 495,158

[52] U.S. Cl. ................................................ 128/85
[51] Int. Cl.² ............................................. A61F 5/04
[58] Field of Search ............. 128/85, 84, 83, 87, 88

[56] References Cited
UNITED STATES PATENTS

| | | | |
|---|---|---|---|
| 412,213 | 10/1889 | Turner | 128/85 |
| 552,143 | 12/1885 | Rankin | 128/85 |
| 1,164,956 | 12/1915 | Nourse | 128/85 |
| 1,539,911 | 6/1925 | Pendergraft | 128/85 |
| 1,573,296 | 2/1926 | Brasell | 128/85 |
| 2,052,990 | 9/1936 | Siebrandt | 128/85 |
| 2,808,052 | 10/1957 | Walchef | 128/85 |
| 3,093,131 | 6/1963 | Kashyap | 128/85 |
| 3,417,748 | 12/1968 | Bimler | 128/85 |
| 3,419,002 | 12/1968 | Santosus | 128/85 |
| 3,848,589 | 11/1974 | Throner | 128/84 C |

*Primary Examiner*—John D. Yasko
*Attorney, Agent, or Firm*—Michael Kovac

[57] ABSTRACT

An extension splint is disclosed as having an elongated frame including a pivoting foot plate and frame brace in order to be readily collapsible as well as being operable in conjunction with means for longitudinally extending the elongated frame above the foot plate in order to apply an extension force to the leg.

12 Claims, 9 Drawing Figures

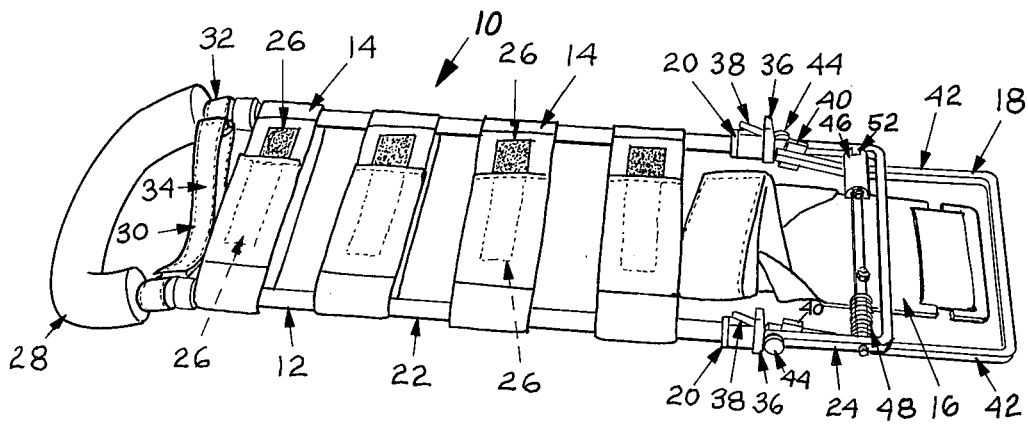
FIG 3
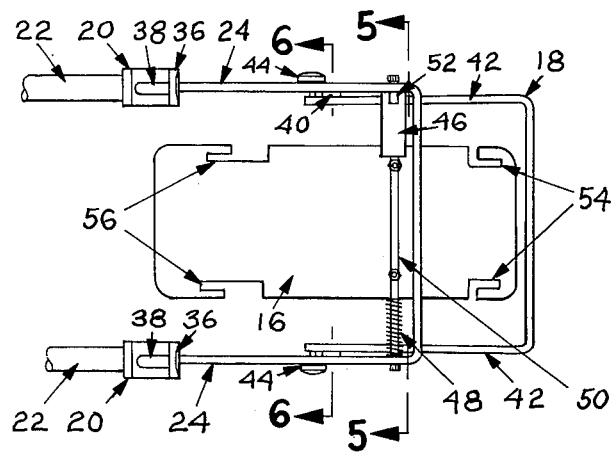
FIG 4
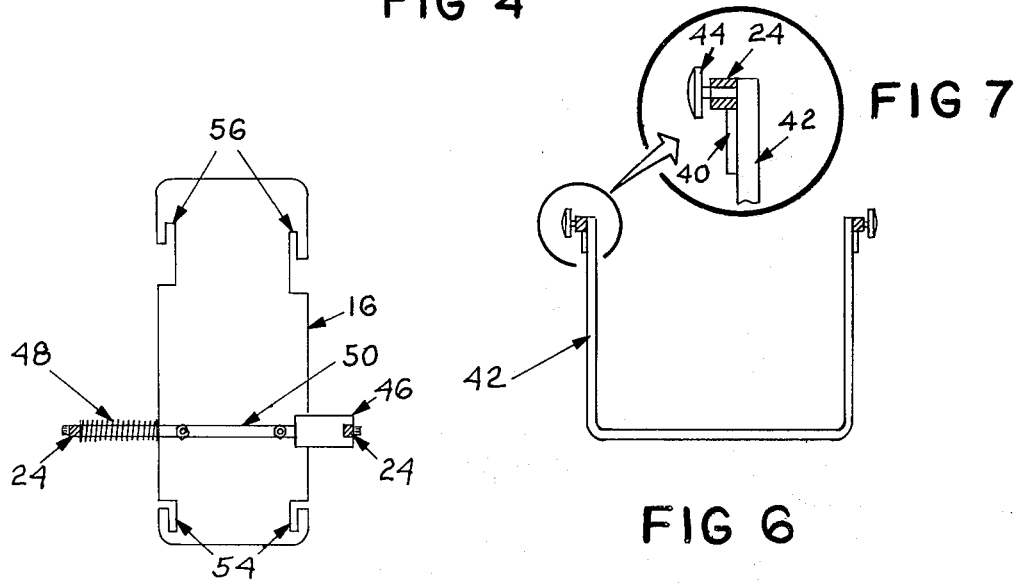
FIG 5
FIG 6
FIG 7

EXTENSION SPLINT

SUMMARY OF THE INVENTION

Medical practitioners and emergency technicians have found that patients with fractures of the hip, the femur and same fractures below the knee should be transported to emergency care facilities with the injured leg or hip in traction. The Instruction Manual on Emergency Care and Transportation of the Sick and Injured states: "When caring for persons with a suspected fracture, it is important to provide for the comfort of the patient. Relief of pain is best obtained by immobilizing (splinting) the fracture with traction."

In addition to care and comfort of the patient, the splint traction system should be simple to operate and use by emergency personnel. The Thomas splint, one of the earliest types of traction splints, uses a U-shaped frame and heel stand with tri-angular bandages which are wrapped around the frame and the leg and foot of the patient in order to apply traction. The difficulty with this splint traction system is that it requires extensive training of emergency personnel and it also takes much more time and effort than is practical or desirable in an emergency situation. Another type of splint traction system known as the Hare splint uses a telescoping frame and leg stand in conjunction with tri-ring ankle and traction straps and leg support straps in order to apply traction. The tri-ring ankle strap and traction strap of the Hare splint are connected to a web roll-up device which exerts a downward pulling force on the ankle and leg of the patient. While the Hare splint has been effective and easier to operate than the Thomas splint, it is not as simple, effective and easy to operate as is desired by emergency personnel.

Difficulty has also been experienced with both the Thomas and Hare splints due to the cumbersome extension of the spling traction system beyond the patient's foot. This results in the splint overhanging the ambulance cot and may also necessitate placing the patient into vehicle feet first. Another difficulty that has been encountered is that the downward pulling force exerted on the foot with the below foot splint traction systems of the Thomas and Hare splints has caused a condition known as "foot drop." This results because the downward pulling force on the foot, in order to apply traction to the leg, allows the foot to be continuously disposed at an abnormal angular position relative to the leg causing unequal forces to be applied to leg muscles. Undesirable "foot drop" creates problems not only in setting the break when a permanent type splint is applied, but also may result in walking difficulties both during and after the healing process.

Accordingly, it is an object of the present invention to provide a new and improved splint device and system which overcomes the aforementioned difficulties.

More specifically, it is an object of the present invention to provide an extension splint system or device which achieves some or all of the following over existing systems or devices: is simpler and faster to use, is safer and more comfortable for the patient, is adjustable for both children and adults, can be folded flat for storage, can be used on bare foot, shoe or boot, prevents foot drop and is otherwise well adapted for intended purposes.

These and other objects and advantages of the present invention are achieved by the provision of an extension splint which includes an elongated frame having releasable leg support means along the length thereof, a pivotable foot plate which is capable of being positioned substantially normal to the frame, a pivotable frame brace extending beneath the frame to support the foot plate above a supporting surface on which the frame rests and means for longitudinally extending the frame above the foot plate in order to apply an extension force to the leg.

BRIEF DESCRIPTION OF THE DRAWINGS

FIG. 3 is a side perspective view of the leg extension splint which illustrates the manner in which the splint may be folded flat for compact storage;

FIG. 4 is a fragmentary top plan view of the foot plate and frame brace portions of the leg extension splint;

FIG. 5 is an end elevational view of the foot plate engaging the elongated frame in locked position as viewed along lines 5—5 of FIG. 4;

FIG. 6 is an end elevational view of the frame brace engaging the elongated frame in locked position as viewed along lines 6—6 of FIG. 4;

FIG. 7 is an enlarged fragmentary end elevational view of frame brace locking means shown in FIG. 6;

DESCRIPTION OF THE PREFERRED EMBODIMENTS

The term "extension" splint or force has been used to distinguish from traction forces applied by below the foot traction systems. As will be seen, the extension force applied through the extension splint of the present invention is an above the foot propelling force which has several important advantages.

Figure 1:
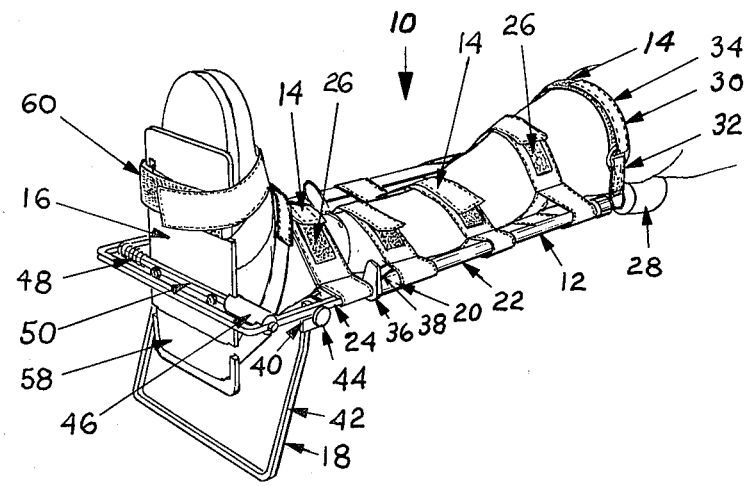
FIG. 1 is a top perspective view of a leg in an extension splint which is constructed in accordance with the teachings of the present invention.
Figure 2:
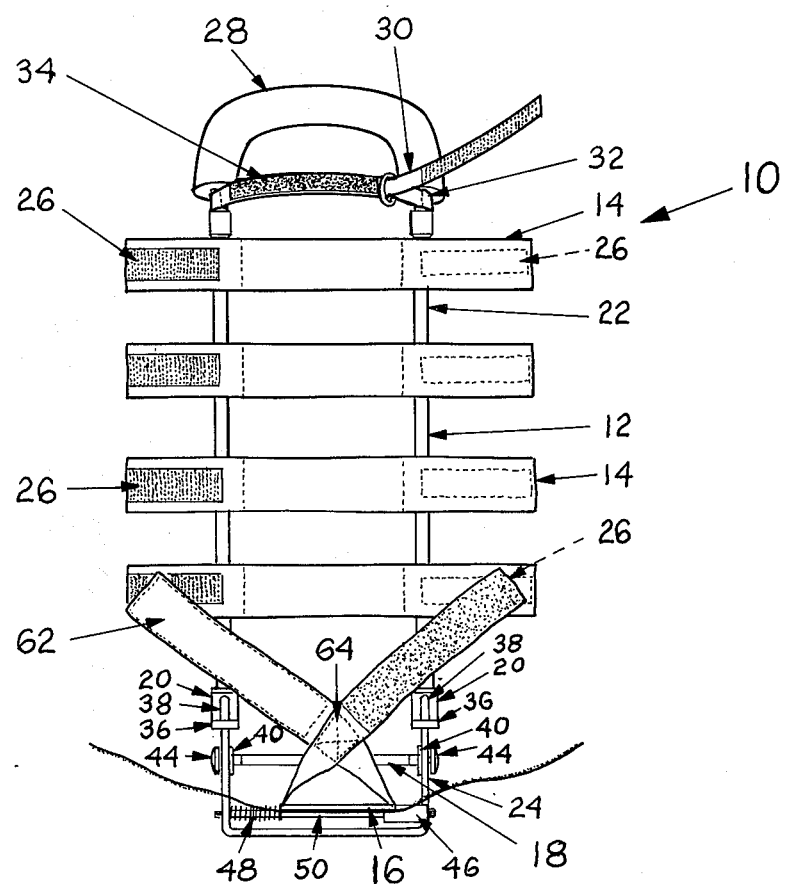
FIG. 2 is a top plan view of the leg extension splint shown in FIG. 1 and illustrating the leg and ankle supporting straps opened up prior to a leg being inserted in the splint.

THe structural components and use of the extension splint of the present invention can best be understood by first referring to FIGS. 1–3 of the drawings. There it will be seen that the extension splint generally designated by the numeral 10 includes an elongated frame 12 with releasable leg support straps 14 along the length thereof, a pivotable foot plate 16 at one end of the frame 12 which can be positioned in the vertical or substantially normal to the frame position as illustrated in FIGS. 1 and 2 or the generally parallel to the frame collapsed position shown in FIG. 3, a frame brace 18 extending beneath the frame which can also be positioned in a vertical or substantially normal to the frame position seen in FIGS. 1–2 or the generally parallel to the frame collapsed position depicted in FIG. 3, and longitudinal extension means 20 for extending the elongated frame 12 above the foot plate 16 in order to apply traction force to the leg.

The elongated frame 12 has telescopically interfitting U-shaped supporting members 22, 24 respectively. U-shaped member 22 carries a plurality (four are illustrated) of leg supporting straps 14 which are attached to the U-shaped supporting member 22. Each of the leg supporting straps 14 have fastening means at the free ends thereof which are preferably in the form of "Velcro" type engaging means 26 on opposite sides of the free ends of the straps 14 as shown in FIG. 2. This will provide releasable engagement of the straps 14 with relatively tight fitting and adjustable features for use and re-use of the splint on patients with different leg sizes.

In order to comfortably and properly position the splint 10 adjacent the patient's leg/hip ball socket, the U-shaped supporting member 22 includes a torous-shaped flexible element 28 which is slightly angularly offset relative to the elongated frame 12. The torous-shaped flexible element 28 is attached to one end of the U-shaped supporting member 22 and is held in position relative to the leg-hip ball socket by the releasable leg supporting strap 30 which includes a ring strap 32 and a "Velcro" type strap 34. After the leg is positioned in the splint 10 with the torous-shaped flexible element 28 adjacent the leg/hip ball socket, the "Velcro" type strap 34 is threaded through the ring of the ring strap 32 and then the "Velcro" type strap is folded back over and attached to itself as best seen in FIG. 1. Between the patient's leg/hip ball socket and foot, the leg supporting strap 14 with "Velcro" type fastening means are used to hold the leg in position relative to the splint 10.

The U-shaped supporting member 22 of the elongated frame 12 further includes the incrementally adjustable locking means 20 for longitudinal extension and retraction of the U-shaped supporting members 22, 24 relative to one another. The U-shaped supporting member 24 has a polygonal cross-sectional configuration and is dimensioned to be slidably received within the U-shaped supporting member 22. The incrementally adjustable locking means 20 are of the type wherein longitudinal extension of the U-shaped supporting members 22, 24 of the frame is provided by pushing the upstanding knobs 36 of the incrementally adjustable locking means 20 to partially telescopically disassociate the U-shaped supporting member 24 from the U-shaped supporting member 22 and thereby longitudinally extend the frame 12. Depressing the levers 38 of the incrementally adjustable locking means 20 will permit partial telescopic association of the U-shaped supporting members 22, 24 for longitudinal retraction of the frame 12.

It is important to note that the incrementally adjustable locking means 20 are positioned above the foot plate 16 in order that extension force can be applied to the leg above the foot plate 16 with the foot held in position by the foot plate straps of the substantially normal to the frame foot plate 16 will be discussed below. The desired amount of extension force can thus be applied without "foot drop" or ambulance cot handling problems as discussed above. The simplicity and ease of incremental adjustment will also be apparent with this structural combination of elements.

The foot plate 16 and frame brace 18 are pivotally attached to the U-shaped supporting member 24 adjacent the foot end of the splint 10. Before the patient's leg is positioned in the splint, the foot plate 16 and frame brace 18 are opened up from the collapsed position shown in FIG. 3 to the vertical or substantially normal to the frame position shown in FIGS. 1–2. Then, the patient's leg is positioned in the splint 10 with the straps opened up as shown in FIG. 2 of the drawings. The frame brace 18 supports the elongated frame 12 and the foot plate 16 above the ground or other supporting surface in order to keep the leg suspended and to facilitate attachment of the various straps of the splint 10.

As best seen in FIGS. 4–7, the foot plate 16 and frame brace 18 include releasable locking means for locking the foot plate 16 and frame brace 18 substantially normal to the elongated frame 12.

The releasable locking means for the U-shaped frame brace 18 includes tab elements 40 which are mounted on the normally spring urged outwardly brace legs 42 adjacent the polygonally configured U-shaped supporting member 24 of the elongated frame 12. The U-shaped frame brace 18 is pivotally mounted to the U-shaped supporting member 24 at the upper free ends of brace legs 42 by the pivotal mounts 44. The polygonal shape and size of the tab elements 40 and their location at the outer upper free ends of the brace legs 42 is such that the tab elements 40 engage the U-shaped supporting member 24 of polygonal configuration along the side sections thereof when the frame brace 18 is generally longitudinally aligned as parallel relative to the elongated frame 12, while the tab elements 40 are positioned for engagement with the bottom sections of the U-shaped supporting member 24 under the spring force of the brace legs 42 when the frame brace 18 is moved to a position substantially normal to the elongated frame 12. As best seen in FIGS. 6–7, the tab elements 40 are positioned below the U-shaped supporting members 24 with their complementary polygonal configurations in non-rotative locking engagement. The frame brace 18 is thus securely locked in position relative to the elongated frame 12. When it is desired to collapse the frame brace 18, it is necessary for opposing inwardly directed force to be applied to the brace legs 42 as the brace legs are rotated to a position where the tab elements 40 engage the side sections of the U-shaped supporting member as illustrated in FIG. 3.

The releasable locking means for the foot plate 16 includes spring biased pawl means in the form of a pawl element 46 and pawl spring 48 which are mounted on a pivotable shaft 50 journalled to the U-shaped supporting member 24 as best seen in FIGS. 3–4 of the drawings. The pivotable shaft 50 is itself attached to the bottom of the foot plate 16 by suitable fastening means in order that the foot plate 16 can pivot relative to the elongated frame 12. As depicted in FIGS. 3–4 of the drawings, the pawl element 48 is fixedly mounted to the pivotable shaft 50 at the upper end thereof while the pawl spring 48 is compressed between the U-shaped member 24 and the foot plate 16 at the lower end of the pivotable shaft 50.

The pawl element 46 includes a slot 52 formed therein adjacent one of the polygonally shaped sections of the U-shaped supporting member 24. The slot 52 has a complementary configured shape relative to the adjacent polygonally shaped section of the U-shaped supporting member in order to permit the slot 52 of the pawl element 46 to engage the adjacent polygonally shaped frame section of the U-shaped supporting member 24 under the force of the pawl spring 50 as seen in FIG. 5 and thereby rotationally lock the foot plate 16 relative to the elongated frame 12 in a position substantially normal to the elongated frame 12. In order to collapse the foot plate 16 to a generally parallel to the frame position as seen in FIGS. 3–4, the foot plate 16 must be shifted to compress the pawl spring 48 to allow disengagement of the pawl slot 52 from the U-shaped supporting member while the foot plate 16 is rotated to the generally parallel to the frame position seen in FIGS. 3–4. If desired, locking means on the pawl element 46 similar to the slot 52 may be provided to lock the foot plate 16 in the collapsed condition, although essentially the same result may be achieved by wrapping the foot straps of the foot plate 16 around the U-shaped supporting member 24 as will be apparent.

As best seen in FIGS. 4–5 the foot plate 16 includes pairs of heel and toe L-shaped slots 54, 56 respectively for receiving heel and toe strap supports 58, 60 respectively as seen in FIGS. 1–3 which also preferably include "Velcro" type fastening means for attaching the patient's bare foot, shoe or boot to the foot plate as shown in FIG. 1. Alternatively, a single foot supporting strap 62 shown in FIG. 2 is preferably used. The single supporting strap 62 is mounted along its mid-portion within the L-shaped heel slots 54 so as to provide two strap sections which are overlapped and attached to one another a predetermined distance from the heel portion of the foot plate 16 as at 64 in order to provide a heel support for the foot plate 16. The unattached remaining portions of the two strap sections of the supporting strap 62 are then brought down along the side of the patient's foot and positioned within the L-shaped toe slots 56 and then wrapped about the patient's toes before being attached to one another by the "Velcro" type fastening means. When a single supporting strap is used, the L-shaped toe slots 56 are preferably offset from one another to facilitate wrapping of the strap 62 about the patient's foot.

Figure 8:
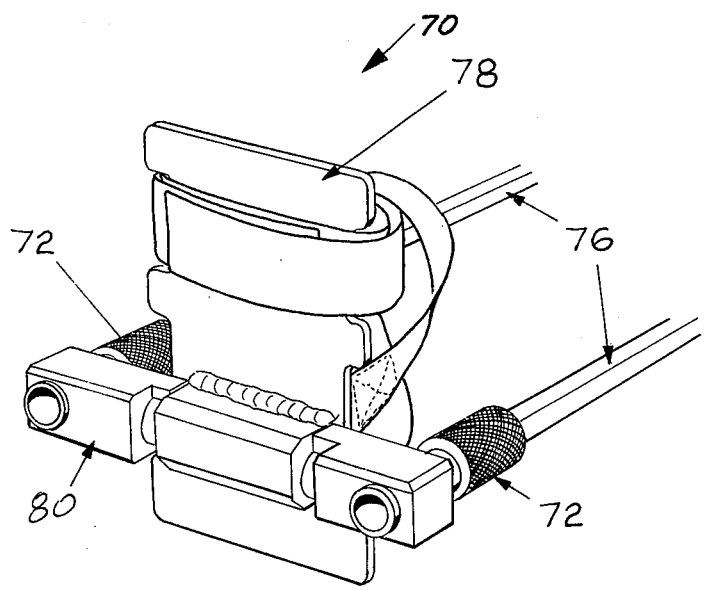
FIG. 8 is a fragmentary end perspective view of another type of leg extension splint which is constructed in accordance with the teachings of the present invention.
Figure 9:
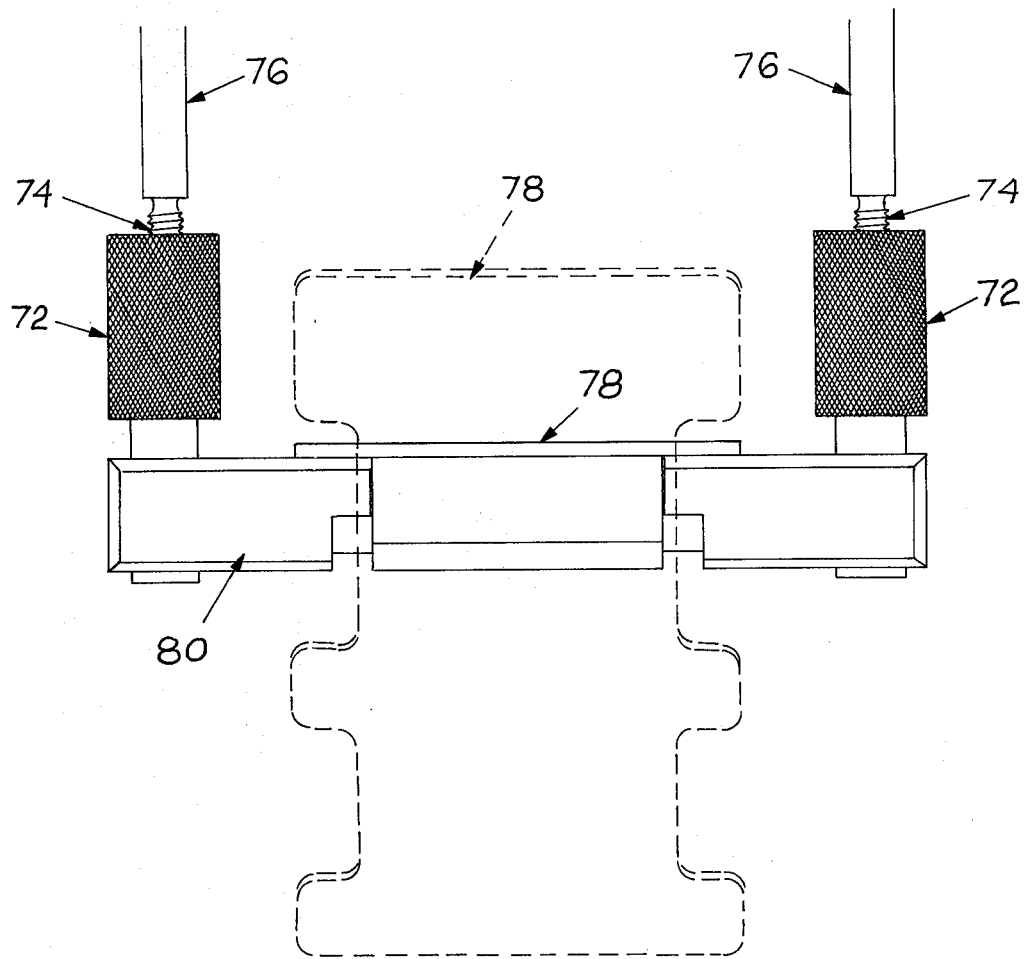
FIG. 9 is an enlarged fragmentary top plan view of the leg extension splint shown in FIG. 8.

Reference is now made to the form of leg traction splint 70 illustrated in FIGS. 8–9 of the drawings. The leg traction splint 70 illustrates a device with several optional or alternative features to the leg traction splint 10 shown in FIGS. 1–7. In the first place, there is illustrated internally threaded hand nuts 72 which are threadably associated relative to externally threaded portions 74 of the partially shown U-shaped supporting member 76. Incremental longitudinal adjustment of the foot plate 78 relative to the U-shaped supporting member 76 may be provided either independently or as an adjunct to the incremental longitudinal adjustment means 20 shown in the FIGS. 1–7 embodiment.

Another optional or alternative feature is the 270° rotating foot plate 78 which can be rotated from the dotted line configuration shown in FIG. 9 where the foot plate 78 overlaps the connecting portion 80 of the U-shaped frame supporting member 76 to a position 270° therefrom as illustrated in the full line configuration of the foot plate in FIGS. 8–9 where further rotation is prevented by the engagement of bottom of the foot plate 78 with the connecting portion 80 of the U-shaped frame supporting member 76.

These optional or alternative features are examples of the type of mechanical features that are within the scope of the present invention.

From the foregoing, it will be appreciated that the extension splint of the present invention is a novel and practical approach for quickly, easily and efficiently applying extension force to a patient's leg while avoiding cumbersome designs that may interfere with the proper setting of the fractured area relative to the patient's foot.

I claim:

1. An extension splint comprising an elongated frame having releasable leg support means along the length thereof, a pivotable foot plate which is capable of being positioned substantially normal to a leg received in said extension splint, a pivotable frame brace extending beneath the frame to support the foot plate above a supporting surface on which the frame rests, and means for applying an extension force to a leg above the foot plate while said leg and foot are held in supported position by said aforementioned components, said last mentioned means including longitudinal frame extension means having manually releasable and incrementally adjustable locking means including generally longitudinally operable extension means and generally transversely operable retraction means.

2. The extension splint as defined in claim 1 including releasable locking means for locking the foot plate and frame brace substantially normal to the elongated frame.

3. The extension splint as defined in claim 2 wherein the releasable locking means for locking the foot plate includes spring biased pawl means which are released for engaging the frame when the foot plate is rotated to a position substantially normal to the frame.

4. The extension splint as defined in claim 3 wherein the spring biased pawl means includes a pawl element and a pawl spring, said pawl element being mounted at one end of a pivotable shaft element that pivotally supports the foot plate on the elongated frame, said elongated frame including polygonally shaped frame elements, said pawl element having a slot formed therein adjacent the elongated frame and being aligned relative to one of said polygonally shaped frame sections when said foot plate is positioned substantially normal to said elongated frame, the slot of the pawl element having a complementary configured polygonal shape relative to an adjacent polygonally shaped frame section in order to permit the pawl element slot to engage the adjacent polygonally shaped frame section under the force of the pawl spring and thereby rotationally lock the foot plate relative to the elongated frame in a position substantially normal to said elongated frame.

5. The extension splint as defined in claim 2 wherein the releasable locking means for locking the frame brace includes spring biased tab means which are released for engaging the frame when the frame brace is rotated to a position substantially normal to the frame.

6. The extension splint as defined in claim 5 wherein the spring biased tab means includes tab elements which are mounted to a U-shaped frame brace adjacent the elongated frame, said U-shaped frame brace being pivotally supported by each of its legs through pivotal mounts extending from the elongated frame, each of the legs of the U-shaped frame brace being normally spring urged outwardly and being spring urged inwardly by the tab elements engaging the elongated frame along side sections thereof when the frame brace is generally longitudinally aligned relative to said elongated frame, said tab elements being positioned for engagement with the frame along bottom sections thereof under the spring force of the legs when the frame brace is moved to a position substantially normal to said elongated frame.

7. The extension splint as defined in claim 2 wherein the elongated frame comprises telescopically interfitting U-shaped supporting members, and said means for longitudinally extending the frame above the foot plate includes incrementally adjustable locking means which are mounted on each of the legs of one of said U- shaped supporting members for releasable locking engagement with the legs of said other U-shaped supporting members.

8. The extension splint as defined in claim 7 wherein the incrementally adjustable locking means for said elongated frame includes generally longitudinally operable extension means which extends the frame in a direction opposite from that in which force is exerted and generally transversely operable retraction means including depressable lever means.

9. The extension splint as defined in claim 8 and further including rotationally longitudinal adjustment means.

10. The extension splint as defined in claim 1 wherein the foot plate includes releasable heel and toe support strap support means.

11. The extension splint as defined in claim 10 wherein at least the releasable heel strap support means comprises a single supporting strap which is mounted along the mid-portion thereof to the heel portion of the foot plate to provide two strap sections, said strap sections being overlapped and attached to one another a predetermined distance from the heel portion of the foot plate in order to provide a heel support for the foot plate.

12. The extension splint as defined in claim 11 wherein the foot plate includes pairs of heel and toe L-shaped slots for receiving the heel and toe strap support means.

* * * * *